(12) United States Patent
Leonard et al.

(10) Patent No.: US 7,324,202 B2
(45) Date of Patent: Jan. 29, 2008

(54) OPTICAL SYSTEM

(75) Inventors: Stephen W. Leonard, Unionville (CA); Ming Gang Xu, Toronto (CA)

(73) Assignee: Novx Systems Inc., Markham, Ontartio (CA)

( * ) Notice: Subject to any disclaimer, the term of this patent is extended or adjusted under 35 U.S.C. 154(b) by 469 days.

(21) Appl. No.: 11/005,325

(22) Filed: Dec. 7, 2004

(65) Prior Publication Data
US 2006/0119845 A1    Jun. 8, 2006

(51) Int. Cl.
*G01N 21/00*    (2006.01)
(52) U.S. Cl. ................... 356/436; 250/458.1; 356/246; 356/440
(58) Field of Classification Search ............... 356/415
See application file for complete search history.

(56) References Cited
U.S. PATENT DOCUMENTS 6,316,774 B1    11/2001    Giebeler et al.
2004/0233545 A1*    11/2004    Jiang et al. ............... 359/726

* cited by examiner

*Primary Examiner*—Tarifur Chowdhury
*Assistant Examiner*—Tara S Pajoohi

(74) *Attorney, Agent, or Firm*—Lynn Schumacher; Hill & Schumacher (57)    ABSTRACT

An optical system is provided for achieving enhanced rejection of scattered excitation light and superior signal-to-noise performance when reading microplate wells. The optical system uses an axial configuration in which the excitation beam incident upon the sample propagates along the axis of the microplate well. Excitation light from a light source, such as a lamp or fiber optic bundle, is collimated into a beam using a lens. A reflective pick-off mirror is then used to reflect the collimated excitation beam upward along the well axis. A focusing lens, with a diameter exceeding the diameter of the collimated excitation beam, is used to focus the excitation beam in the well. The same broad lens is used to collimate the emitted fluorescent light, of which a large percentage propagates axially past the pick-off mirror towards a second focusing lens that focuses the emission beam onto the face of a fiber optic bundle. The emitted light is later filtered and detected using at a position that is optically shielded from the aforementioned optical system. The optical system is incorporated into a microplate reader or automated assay instrument in order to provide a compact assembly for sensitive fluorescence measurements either above or below the microplate. The optical system further enables the simultaneous measurement of absorbance and fluorescence in a compact optical configuration.

27 Claims, 8 Drawing Sheets

(A)          (B)

PRIOR ART

PRIOR ART

Figure 2

PRIOR ART

OPTICAL SYSTEM

FIELD OF THE INVENTION

The present invention is related to an optical system for achieving enhanced rejection of scattered excitation light and superior signal-to-noise performance when reading microplate wells and more particularly the present invention relates to an optical system which enables the simultaneous measurement of absorbance and fluorescence in a compact optical configuration.

BACKGROUND OF THE INVENTION

Optical measurements are routinely used to detect and quantify the presence of species in chemical and biological samples. The most common forms of optical measurement are absorption, fluorescence, and luminescence. In absorbance measurements, the degree of attenuation caused by optical absorption is related to the concentration of the species of interest. Fluorescence measurements involve exciting the sample via short-wavelength optical radiation and measuring the optical power of longer-wavelength fluorescence. Luminescence measurements rely on the measurement of light emitted by the sample without the presence of excitation light, most often caused by a chemical reaction.

In modern analytical instruments, small sample volumes are arranged in a multiple-well plate known as a microplate, usually comprised of 96, 384 or 1536 individual wells. A typical instrument optically scans the wells and detects optical power. The optical power is then related to the sample concentration using a known functional relationship. Fluorescence is most commonly used as a sensitive means to detect very low sample concentrations and maintain a wide dynamic range.

Despite the large number of patents pertaining to fluorometric instruments, little attention has been paid to the elimination of stray excitation light, which can cause significant signal degradation. Stray light can arise from a multitude of sources, including lens surfaces, microplate window surfaces, and scattering within the optical system. However, the dominant source of stray light in a microplate fluorometer is usually the liquid meniscus at the sample-air interface. This source of stray light is particularly difficult to reject since the meniscus can vary in position (due to different sample volumes) and curvature (due to different surface properties). Most importantly, a spatially extended beam impinging on the meniscus results in a wide angular bandwidth upon reflection, making it difficult to achieve rejection by simple baffling alone. One patent that has attempted to improve upon the prior art in this regard is listed below.

U.S. Pat. No. 6,316,774, titled "Optical System for a Scanning Fluorometer", discloses an optical instrument for the measurement of absorbance and fluorescence from microplates. The patent teaches a method of measuring fluorescence from above and below a microplate well using elliptical reflective mirrors that are arranged in a manner in which the collection of excitation beam scatter is reduced. Unfortunately, the invention only succeeds in eliminating the collection of scattered excitation light for a very limited range of sample volumes and meniscus curvatures.

It would be very advantageous to provide an optical system that could broadly be used to reduce interference arising from liquid scattering of excitation light from a liquid meniscus in any type of optical system used for optical analysis of liquids contained in vessels, which advantageously could be integrated into a microplate reader or automated assay instrument in order to provide a compact assembly for sensitive fluorescence measurements that avoids or reduces the interference of scattered light from the liquid meniscus.

SUMMARY OF THE INVENTION

Accordingly, an invention is provided in which a compact optical system is used to measure fluorescence from a microplate well with exceptional rejection of scattered excitation light. This is accomplished using an axial configuration in which the excitation beam incident upon the sample propagates along the axis of the microplate well. Excitation light from a source, such as a lamp or fiber optic bundle, is collimated into a beam using a lens. A reflective pick-off mirror is then used to reflect the collimated excitation beam upward along the well axis. A focusing lens, with a diameter exceeding the diameter of the collimated excitation beam, is used to focus the excitation beam in the well. The same broad lens is used to collimate the emitted fluorescent light, of which a large percentage propagates axially past the pick-off mirror towards a second focusing lens that focuses the emission beam onto the face of a fiber optic bundle. The emitted light is later filtered and detected using methods known to those skilled in the art at a position that is optically shielded from the aforementioned optical system. The optical system is incorporated into a microplate reader or automated assay instrument in order to provide a compact assembly for sensitive fluorescence measurements either above or below the microplate.

Thus, the present invention provides an optical system for measuring fluorescence from a liquid contained in a vessel, comprising:

a) a light source and a first lens for collimating excitation light from said light source into a beam of excitation light, a fully reflective mirror positioned to receive and redirect the beam of excitation light in a first direction along an axis of a vessel located in a vessel holder located on one side of said fully reflective mirror, a second lens positioned along said axis on said one side of said vessel between said fully reflective mirror and said vessel for focusing said beam of excitation light onto said vessel and collimating light emitted from a liquid in said vessel;

b) a third lens symmetrically disposed with respect to said axis of said vessel and on a second side of said fully reflective mirror, for focusing light collimated by said second lens onto a first detection means; and c) said second lens having a diameter larger than a cross sectional area of said fully reflective mirror transverse to said axis such that excitation light scattered from refractive surfaces within the vessel including a liquid meniscus is rejected by said fully reflective mirror, but some fluorescent light emitted by the liquid in said vessel bypasses the fully reflective mirror and is focused onto the detection means by said third lens.

The optical system may include a second detection means positioned relative to said vessel so that the optical power of the excitation beam that propagates axially through the microplate well can be measured on the opposing side of the microplate in order to provide a measurement of absorbance. A dual mode system is therefore enabled by the invention in which absorbance and/or fluorescence can be measured simultaneously.

The size of the optical source and the magnification of the excitation beam path optics may be chosen in such a way as to produce a small focused spot in the center of the microplate well. This small spot, preferably less than 2 mm, causes the excitation beam to encounter only the zone within the center of the liquid meniscus having a near-axial surface normal. The axial surface normal of the central meniscus causes the angular bandwidth of the reflected excitation cone to be narrow, enabling rejection via apertures within the optical system.

A limiting aperture may be used to produce a low numerical aperture excitation beam. A low numerical aperture is desirable for two distinct reasons. Firstly, the low numerical aperture makes the excitation beam more amenable for absorption measurements, since the optical path through the well is made more columnar and less conical. Secondly, the lower angular bandwidth of the excitation beam incident on the well also serves to lower the angular bandwidth of the scattered excitation light cone produced by the meniscus. The limiting aperture also helps to eliminate multiple reflections caused by the lens collimating the excitation beam from the light source or fiber optic bundle.

The pick-off mirror is preferably chosen to have a diameter larger than that of the collimated excitation beam in order to reject a substantial amount of the low numerical aperture component of the scattered excitation light. The rejection of this component of the scattered excitation light via a mirrored surface removes a large fraction of the scattered excitation light from the optical system.

A shadow disc, comprising a thin opaque disc that preferentially absorbs light and reflects diffusely, may be placed immediately above the second focusing lens (the lens that focuses the emitted light) in order to stop scattered excitation light from reaching the focus. As a result of the aforementioned aspects that decrease the angular bandwidth of the scattered excitation light, the scattered excitation cone (the outer regions of which are produced by the meniscus) collimates to a diameter that can be less than that of the first lens (the lens that focuses the excitation beam and collimates the emitted light). By choosing a shadow disc that has a diameter that is slightly larger than the diameter of the collimated scattered excitation beam but less than that of the upper lens, the scattered excitation light is very effectively prohibited from directly scattering to the focus. Finally, since the scattered excitation beam is in many cases slowly converging after propagating through the first lens, a free propagation path between the first lens and the shadow disc can further increase the power of the collected emission light relative to the scattered excitation light.

Thus, in another aspect of the invention there is provided an optical system for measuring fluorescence, comprising:

a) a light source and a first lens for collimating light from said light source into a beam of light, a reflective mirror positioned to receive and redirect the beam of light in a first direction along an axis of a vessel located on one side of said reflective mirror, a second lens positioned along said axis on said one side of said vessel between said reflective mirror and said vessel for focusing said beam of light onto said vessel and collimating light emitted from a liquid in said vessel;

b) a third lens symmetrically disposed with respect to said axis of said vessel and located on a second side of said reflective mirror, for focusing light collimated by said second lens onto a first detection means; and c) a shadow disc symmetrically disposed with respect to said axis located between the said reflecting mirror and said third lens, wherein a diameter of said shadow disc is greater than that of a cross sectional area of said fully reflective mirror transverse to said axis but less than the diameter of said second lens such that excitation light scattered from refractive surfaces within the vessel including a liquid meniscus is rejected by said shadow disc, but some fluorescent light emitted by the liquid in said vessel bypasses the fully reflective mirror and is focused onto the detection means by said third lens.

The present invention also provides an embodiment of an optical system in which the aforementioned lenses are replaced with mirrors that simplify the design and eliminate chromatic aberrations. The low numerical aperture lens that had collimated the source and the reflecting mirror may be replaced with a single concave mirror that refocuses the excitation beam into the liquid containing vessel along an axis of the vessel. The upper focusing lens is replaced with an off-axis parabolic mirror. This mirror collimates the emitted light and reflects it in a direction normal to the well bottom. This mirror has a hole cut through it in order to pass the focusing excitation beam that is directed along the well axis. An aspheric lens may then be used to focus the light emitted from the liquid onto a detector, or a fiber bundle optically coupled to the detector. In front of the aspheric lens there may be included a shadow disc, which again serves to reject the narrow beam of collimated (or slowly converging) scattered excitation light. The aspheric lens may also be replaced with an on- or off-axis parabolic mirror.

Thus, there is provided an optical system for measuring fluorescence from a liquid contained in a vessel, comprising:

a) a light source and a first concave mirror for directing and focusing excitation light beam from said light source onto said vessel, along an axis of said vessel located in a vessel holder;

b) a second concave mirror for collimating and redirecting light emitted from the liquid in said vessel along another axis, said second concave mirror being located between said vessel and said first concave mirror, said second concave mirror including a hole through which the excitation light beam reflected by the first concave mirror passes;

c) a directing and focusing means for directing and focusing light collimated and redirected from said second concave mirror onto a detection means; and d) wherein excitation light scattered from refractive surfaces within the vessel including a liquid meniscus passes through said hole, but some fluorescent light emitted by the liquid in said vessel is reflected by the second concave mirror and is focused onto the detection means by said directing and focusing means.

The present invention also provides a method for measuring fluorescence from a liquid contained in a vessel, comprising the steps of:

a) collimating light from a light source into a beam of excitation light and directing the collimated beam of excitation light toward a fully reflective mirror which receives the collimated beam of excitation light and redirects it in a first direction along an axis of a vessel located in a vessel holder located on one side of said fully reflective mirror, focusing said collimated beam of excitation light onto said vessel and collimating light emitted from a liquid in said vessel and directing the collimated light emitted from the vessel in a direction 180 degrees to said first direction back along said axis, wherein said step of focusing said collimated beam of excitation light onto said vessel and collimating light emitted from a liquid in said vessel is performed using a first focusing and collimating means; and b) focusing the collimated light emitted from the vessel onto a first detection means located on another side of said fully reflecting mirror using a second focusing means, wherein said first focusing and collimating means has a diameter larger than a cross sectional area of said fully reflective mirror transverse to said axis such that excitation light scattered from refractive surfaces within the vessel including a liquid meniscus is rejected by said fully reflective mirror, but some fluorescent light emitted by the liquid in said vessel bypasses the fully reflective mirror and is focused onto the detection means by said second focusing means.

The present invention also provides a method for measuring fluorescence from a liquid contained in a vessel, comprising the steps of:

a) directing and focusing excitation light from a light source onto a vessel along an axis of said vessel using a first concave mirror;

b) collecting, collimating and redirecting light emitted from the liquid in said vessel along another axis using a second concave mirror, said second concave mirror being located between said vessel and said first concave mirror, said second concave mirror including a hole through which the excitation light beam reflected by the first concave mirror passes; and c) directing and focusing light collimated and redirected from said second concave mirror onto a detection means, wherein excitation light scattered from refractive surfaces within the vessel including a liquid meniscus passes through said hole, but some fluorescent light emitted by the liquid in said vessel is reflected by the second concave mirror and is focused onto the detection means by said directing and focusing means.

A further understanding of the functional and advantageous aspects of the invention can be realized by reference to the following detailed description and drawings.

BRIEF DESCRIPTION OF THE DRAWINGS

The invention will now be described, by way of non-limiting examples only, reference being had to the accompanying drawings, in which.

DETAILED DESCRIPTION OF THE INVENTION

Figure 1:
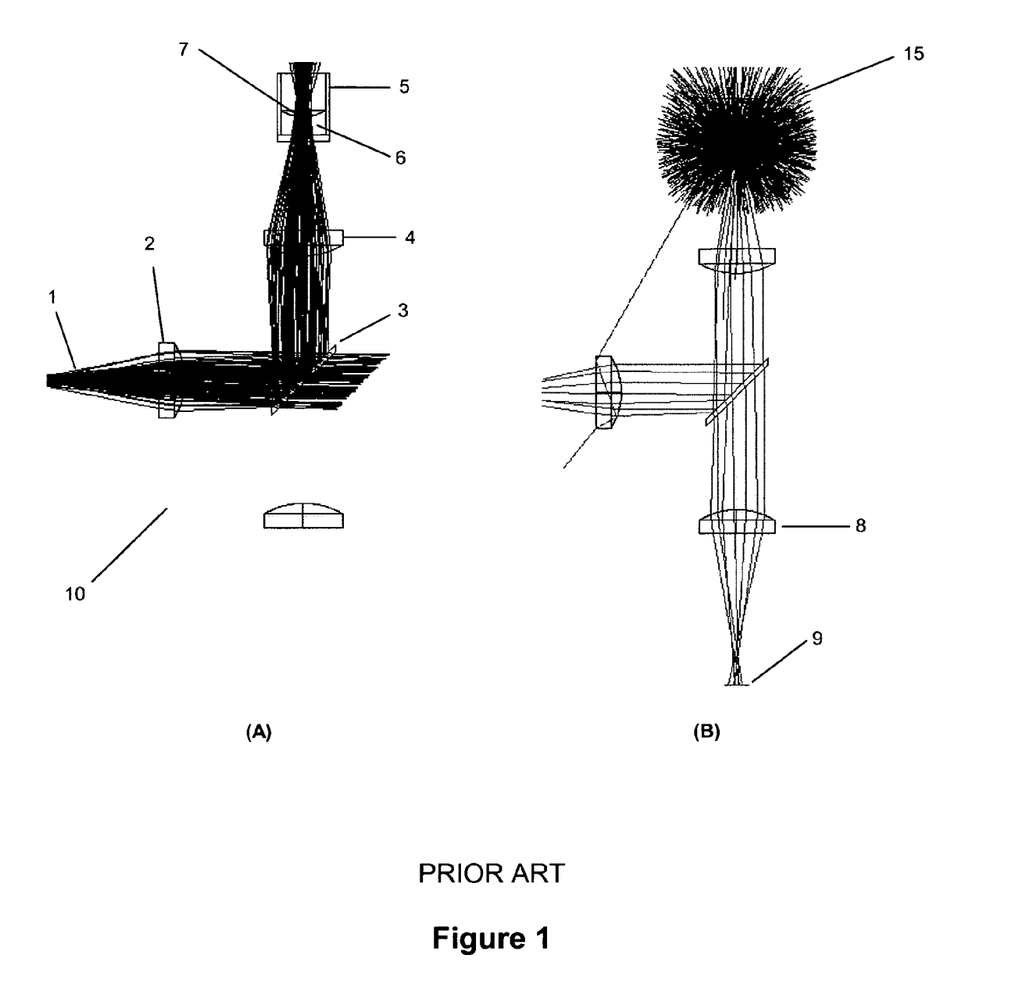
FIGS. 1A and 1B schematically illustrate a typical prior art optical system used to measure fluorescence in the prior art, with FIG. 1(A) showing the excitation light beam path and FIG. 1B showing the emission beam path.

Referring to FIG. 1, there is a schematic of a conventional optical system 10 for measuring fluorescence from a microplate well or any other type of liquid sample containing vessel. In FIG. 1A, an optical source 1, usually either a filtered light source or a fiber optic bundle delivering filtered light, is collimated by lens 2 and reflected to the microplate well 5 by beamsplitter 3. A second lens 4 focuses the excitation light onto the microplate well, where it is focused into the fluorescent sample liquid 6 with meniscus 7. In FIG. 1B, the emitted light from the sample 15 is collimated by lens 4, propagates through beamsplitter 3 and is focused with lens 8 to a focal point 9. If no emission filter is used between beamsplitter 3 and lens 8, then focus 9 is usually coincident with the aperture of a fiber bundle that delivers the emitted light to a remote filtering and detection location. Otherwise, a detector is placed at the focus 9 and the optical power of the emitted light is measured.

It will be appreciated that while the present invention is being described using liquid vessels which are microplate wells, the optical system disclosed herein is may be used with any type of liquid containing vessel in which scattering of light by the liquid meniscus may be problematic.

Figure 2:
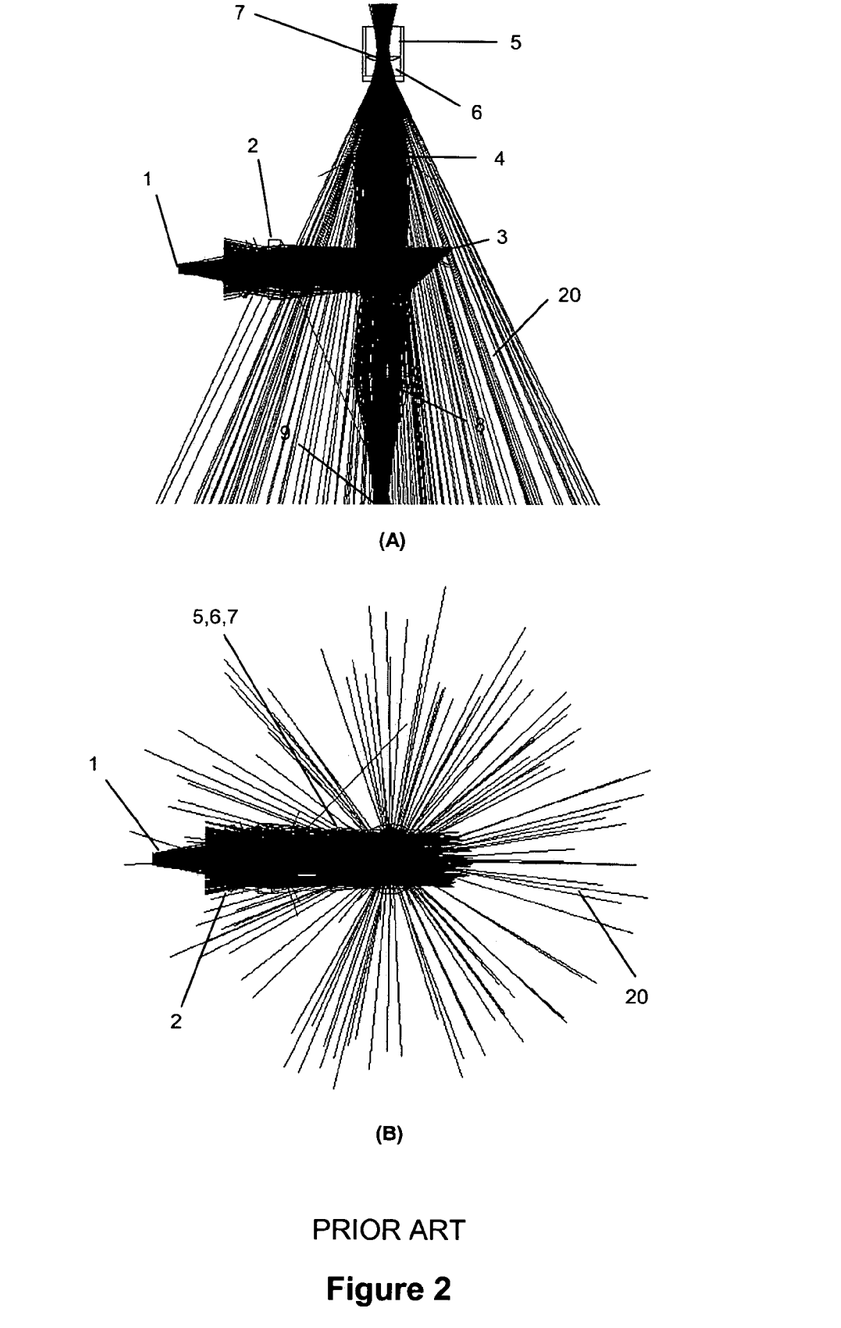
FIGS. 2A and 2B are illustrations of the excitation beam rays scattered from the meniscus for the prior art optical system of FIG. 1 with FIG. 2A showing a side view and FIG. 2B showing an overhead view.

FIGS. 2A and 2B show the geometric paths taken by excitation beam rays as they scatter off of the reflective surfaces of the optical system shown in FIG. 1. FIG. 2A illustrates excitation beam scattering from the side view and FIG. 2B provides an overhead perspective. FIGS. 2A and 2B clearly reveal the meniscus 7 as the dominant source of scattering in this configuration. Although the well bottom and focusing lens 4 produce a retro-reflection of the incident beam along its incoming path, the curvature of the meniscus 7 causes the scattered rays to fan out over a wide angular zone. The meniscus therefore acts as a virtual source of excitation light within the fluorescent zone of the liquid sample 6. Even if one blocks the primary beam path through the beamsplitter and collects light emitted in the outer angular zones, a large percentage of scattered excitation light will still corrupt the measured signal.

Figure 3:
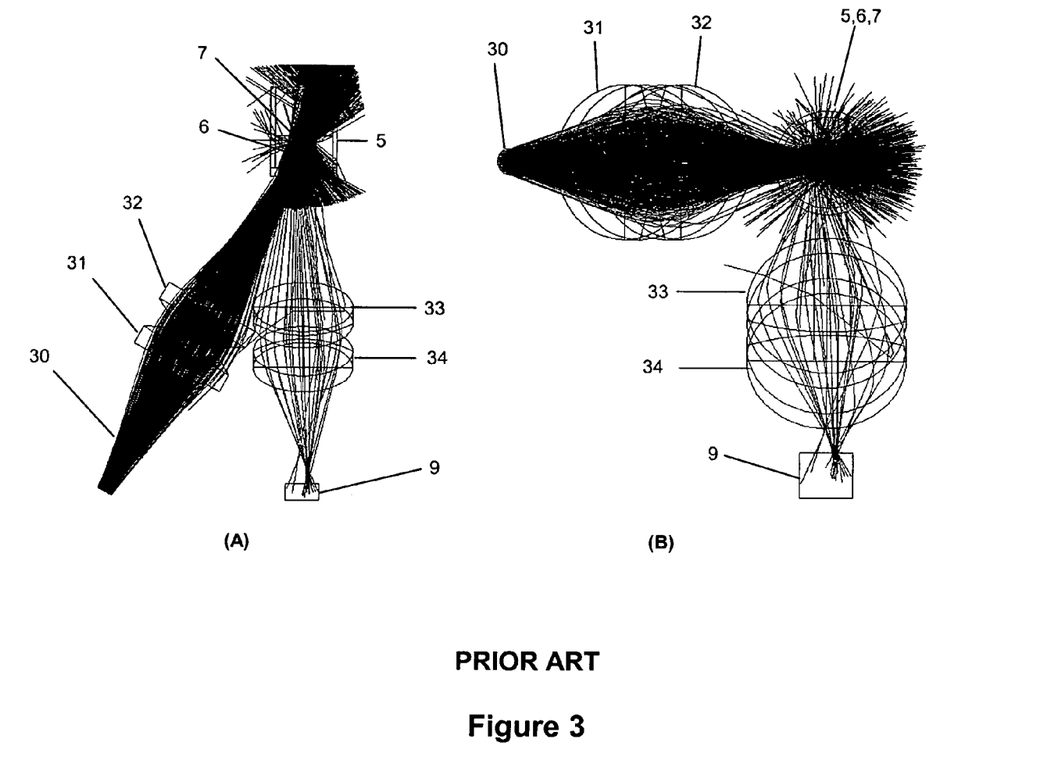
FIGS. 3A and 3B show an alternate prior art optical system in which the excitation and emission beam axes are not parallel to the well axis in which the excitation and emission beam paths are also orthogonal when projected onto the horizontal plane, with FIG. 3A showing a side view of the scattered excitation rays and FIG. 3B showing overhead views.

An alternative prior art optical system that improves upon that of FIG. 1 is shown in FIGS. 3A and 3B. This optical system employs a non-axial configuration in order to reduce the amount of scattered excitation light that reaches the detector. Both the excitation axis and emission axis are oriented at an angle of 30° relative to the well axis, and the excitation and emission axes are orthogonal when projected onto the horizontal plane. The source light 30 is collimated and focused onto the well 7 by lenses 31 and 32, respectively. Lenses 33 and 34 collect and re-image the fluorescent light emitted by the well. In this configuration, the portion of the excitation beam that scatters off of the well bottom is advantageously directed away from the solid angle subtended by the detector.

Although the design is well suited for eliminating the collection of scattered excitation light from flat surfaces, it fails to sufficiently discriminate between emitted and scattered light when a curved surface is present. FIGS. 3A and 3B illustrate the poor performance obtained with a curved meniscus from the perspectives of a FIG. 3A showing the side view and FIG. 3B showing the overhead view. Although most rays scatter away from collimating lens 33, a sizable fraction is scattered within the collection solid angle. These rays are eventually imaged onto the focus 9 and result in a decreased signal-to-noise ratio.

Referring now to FIGS. 4A, 4B and 4C, there is shown an optical system in accordance with the present invention to obtain a dramatic reduction in the amount of collected scattered excitation light. FIG. 4A illustrates the propagation of the excitation beam through the system without considering scattering. Lens 41 collimates the light from light source 40 into a beam that is passed through aperture 44. This aperture serves to reduce the diameter of the collimated beam and thus lower the numerical aperture of the beam as it is focused onto the microplate well. The fully reflective pick-off mirror 42 redirects the beam upwards along the axis of the microplate well. The excitation beam is then focused using lens 43 onto the microplate well 5. The beam passes through the well and is detected above the well by absorbance detector 48. In FIG. 4B, the collection of emitted rays from the optically excited fluorescent liquid 6 is shown. Although many of the small-angle emitted rays 49 are rejected by the pick-off mirror 42, the majority of the emitted power that is collected by the upper lens 43 passes the pick-off mirror. The shadow disc 45 further attenuates the collimated emission beam, but allows a thin collimated ring to pass onto the lower lens 46, which focuses the emission beam to focal point 47. The diameter of the lower lens 46 is preferably greater than or equal to the diameter of the upper lens 43.

In a preferred embodiment, the light source 40 is preferably a narrow band source, such a fiber optic bundle that delivers light from a remote source and filtering subsystem. Alternatively, a broadband light source can be filtered within the inventive optical system by placing a filter between the aperture 44 and the fully reflective pick-off mirror 42. Also, in a preferred embodiment, a light conduit (not shown) resides at the focal point 47. This conduit can be, for example, a fiber optic bundle for the delivery of the collected fluorescent light to a remote filtering and detection subsystem. Alternatively, a filter can be placed between the upper lens 43 and the lower lens 46, whereby the filtered fluorescence light is detected locally by a detector placed at the focus 47.

The advantageous aspect of the invention is shown in FIG. 4C, in which the scattered rays from the excitation beam are depicted. The majority of the scattered rays are produced by the liquid meniscus 7, which again acts as a source of a cone of scattered light. All scattered rays are collimated by the lens 43. However, since the mirror 42 is now entirely reflecting rather than partially reflecting, a large portion of the scattered rays are deflected horizontally and do not reach the focal point 47. The scattered rays produced by the upper surface of lens 43 and the bottom of the microplate well 7 are thus entirely removed by the pick-off mirror 42. The large-angle scattered rays (produced by the meniscus) that do succeed in bypassing the pick-off mirror 42 are blocked by shadow disc 45, which preferably absorbs all rays that impinge upon it. The only excitation rays that do travel beyond the shadow disc 45 originate at the lower surface of the upper lens 43. Since these rays are not in a conjugate image plane of the microplate well, they are not imaged onto the final focus 47 and are therefore of no consequence.

It can also be seen in FIG. 4C that the collimated scattered excitation rays are not perfectly collimated, but slightly converge after passing through lens 43. It is therefore evident that placing the shadow disc 45 further away from the lens 43 improves the performance of the system in that the ratio of the detected emission power to the detected scattered excitation power is enhanced. This ratio forms a useful figure of merit for the optical system and is henceforth referred to as the signal-scattering extinction ratio (SSER). In a preferred embodiment, the spatial separation between the lens 43 and the shadow disc 45 is greater than or equal to the diameter of the lens 43.

In order to obtain a very high SSER over a wide range of sample volumes (i.e. meniscus heights) and meniscus curvatures, the size and angular bandwidth of the incident excitation beam must be carefully designed. In particular, the size of the beam focus must be kept to a minimum so that the spatial extent of the beam only samples the central region of the meniscus. A broad, extended beam will sample a wide range of curvatures, producing a deleterious wide cone of scattered excitation light. A tight focus, with a size preferably less than 25% of the diameter of the meniscus, will produce a reflection with a relatively narrow angular bandwidth. In this context, the diameter of the meniscus is defined as the perimeter of the meniscus at its point of contact with the inner surface of the vessel. In the case of a 96-well microplate, the size of the beam focus is preferably 2 mm or less. This narrow cone of scattered excitation light is more amenable to complete rejection by the shadow disc 45.

The requirement that the spatial extent of the beam be less than 2 mm over a wide range of fluid volumes also implies that the numerical aperture of the incident beam also be low. A low numerical aperture results in a beam that is only weakly converging and diverging on opposite sides of the focus. The numerical aperture of the excitation beam is preferably less than 0.20 in order to obtain a high SSER. Such a low numerical aperture also facilitates the measurement of absorption, which is preferably performed with a collimated beam passing through the sample. In practice, a low-numerical aperture beam is also useful for absorption measurements. The combination of a small focus and low numerical aperture provides a near-collimated beam within the well that is not clipped by the sides of the well upon transmission.

A further requirement for a high SSER is the need for accurate placement of the excitation beam focus within the center of the microplate well 5. A deviation of the focal point from the well center will result in the beam encountering a point on the meniscus where the central surface normal is not directed along the well axis. This in turn causes the scattered excitation cone to be deflected along a non-axial direction and some scattered rays may bypass the shadow disc 45 and reach the final focus 47. A positional tolerance of ±0.25 mm is preferred for optimal performance. This requirement also assists in providing an optimal absorbance measurement, since deviations of the beam relative to the meniscus center can cause path length variations that produce absorption errors.

The diameter of the shadow disc 45 must be sufficiently large to intercept all excitation rays that are directly scattered by the meniscus. The shadow disc is preferably made of a material that absorbs all the light that impinges upon it.

A maximum limit for the diameter is set by the diameter of the upper lens 43, which defines the width of the collimated emission light. The diameter of the shadow disc is preferably at least 75% of the diameter of the lens 43. Although this attenuates the emission power, the attenuation is proportion to the square of the diameter ratio, resulting in a loss of only approximately 50% or 3 dB. The corresponding gain in the SSER can exceed three orders of magnitude. Alternatively, the shadow disc can be removed from the optical system and the fully reflective pick-off mirror 42 can be chosen to have a sufficiently large diameter (preferably at least 75% of the diameter of the lens 43) to redirect a substantial amount of the scattered excitation beam away from the detector.

A preferred embodiment of the invention is henceforth disclosed, in which inexpensive stock optical components are used in the assembly of an optical system designed to measure 96-well microplates. FIGS. 5A and 5B illustrates the optical system and three-dimensional views of the excitation (FIG. 5A) and emission paths (FIG. 5B). The optical components are housed in a black anodized aluminum housing 62, preferably made from multiple parts for ease of assembly.

A fiber optic bundle is inserted into the upper horizontal arm 63, projecting a diverging excitation beam axially along the arm. The excitation light 50 emitted by the bundle has been obtained from either a laser or broadband optical source remotely from the inventive optical system using methods known in the prior art. The fiber optic bundles are preferably made from silica, with a numerical aperture of 0.22. The diameter of the bundle aperture is preferably 1 mm, with 19 fibers with a core diameter of 200 µm arranged in a hexagonal pattern.

A plano-convex lens 51 with a ½ inch diameter and a focal length of 20 mm is employed to collimate the excitation beam. Aperture 52 reduces the diameter of the collimated beam to 5 mm. Pick-off mirror 53 is a BK7 rod mirror with one side polished at an angle of 45° relative to the rod axis. The polished side is coated with aluminum to form a broadband mirror. The diameter of the rod is 10 mm. Such rod mirrors have recently become commercially available and are very inexpensive. The pick-off mirror 53 is attached to optical window 55, which is preferably made of BK7 glass. The thickness of the window is 3 mm and the diameter is 30 mm. The pick-off mirror 53 directs the excitation beam upwards along the well axis, where it is intercepted by aspheric lens 54. This lens is preferably an inexpensive stock molded-glass aspheric lens with a diameter of 30 mm and an effective focal length of 27 mm. The spatial offset between the reflective pick-of mirror 53 and the aspheric lens 54 is preferably less than 2 mm. The excitation beam is focused onto the optical well with a numerical aperture of 0.18. The excitation beam passes through the well 5 and its optical power upon transmission is directly measured with a large-area silicon detector 61 on the opposite side of the microplate well. The absorbance of the liquid sample 6 is measured in this fashion by referencing the measured optical power to the optical power without the microplate present in the conventional manner.

If the liquid sample is fluorescent, the emitted light is collimated by lens 54, where it forms an axial beam that propagates towards the pick-off mirror 53, as in FIG. 4B. Although the pick-off mirror attenuates the central portion of the emission beam, most of the power collected by lens 54 is retained. The beam passes through optical window 55 and is partially attenuated by shadow ring 57. The shadow ring 57 is supported by rod 56, which is attached to the bottom of optical window 55. The diameter of the shadow ring is 21 mm, which shadows approximately 50% of the area of the initial collimated emission beam. The remaining ring of emission light is focused by lower aspheric lens 58, which preferably is a stock molded glass aspheric lens with a diameter of 38 mm and a focal length of 30 mm. The emission light is then reflected by aluminized elliptical mirror 59, which deflects the focusing beam again into the horizontal plane where it is focused onto the end face of fiber optic bundle 60. The elliptical mirror 59 is preferably an inexpensive aluminized secondary mirror of the type used in Newtonian reflector telescopes. The emission bundle 60 is preferably an inexpensive borosilicate glass bundle with a numerical aperture of at least 0.4 and an end face diameter of 4 mm. The overall collection efficiency of the optical system is approximately 1%.

Figure 6:
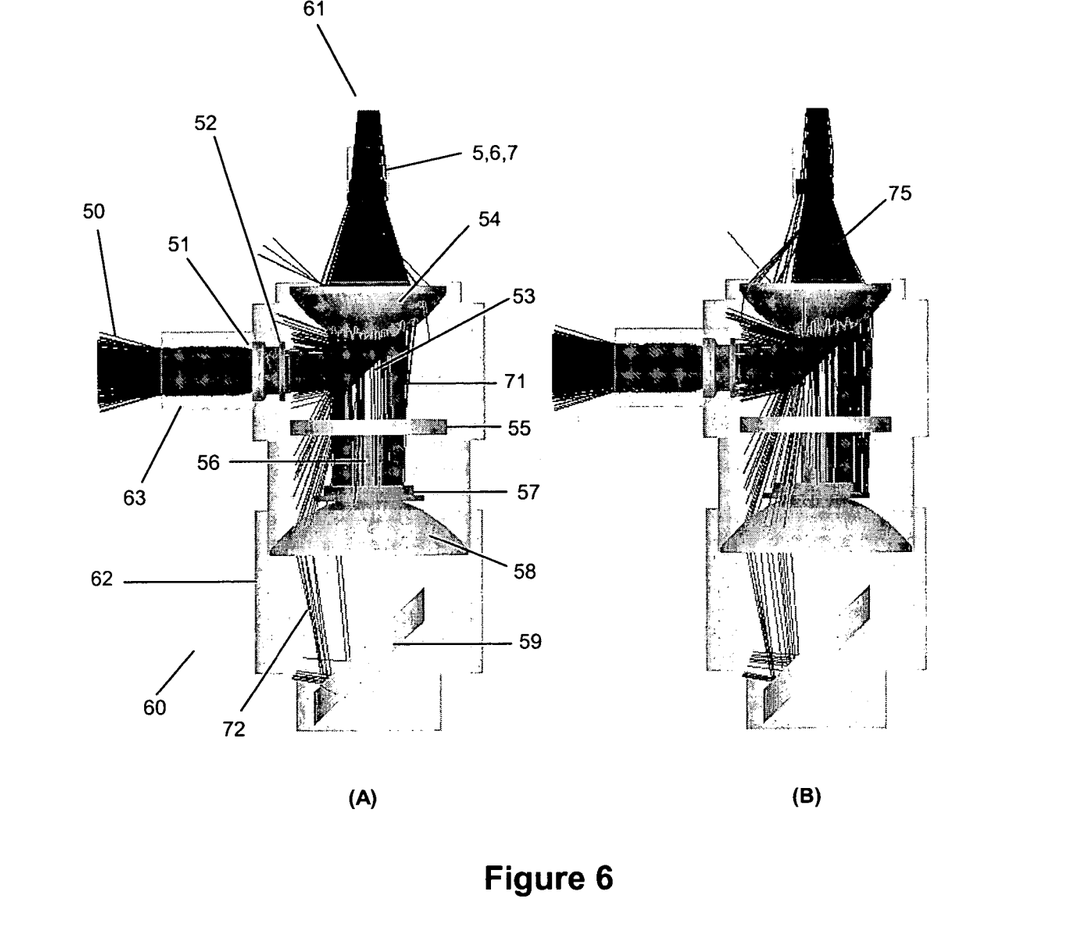
FIGS. 6A and 6B show three-dimensional illustrations of the scattered excitation ray paths in the preferred embodiment of the invention, with FIG. 6A showing an embodiment in which an excitation beam is centered on the well and FIG. 6B showing an embodiment in which the excitation beam is misaligned by 0.4 mm from the well center.

FIG. 6A illustrates the performance of the optical system in terms of the rejection of scattered excitation light. The Figure displays all rays that retain more than 0.8% of the original power, which translates into all directly scattered rays. Rays originating from higher-order scattering processes are not shown. The cone of scattered excitation light 71 from the meniscus is clearly seen emanating from the microplate well 5, whereupon the rays are collimated by the lens 54. Again, the collimated rays slightly converge as they travel away from lens 54. These rays are intercepted by shadow disc 57 and are prohibited from reaching the aperture of the emission bundle 60. Although a group of rays 72 do succeed in bypassing the shadow disc, they are produced by scattering at the bottom side of lens 54 and are not imaged onto the emission bundle 60. These rays therefore do not cause a decrease in the SSER.

The case of a decentered well is considered in FIG. 6B, in which the well axis and the optical system axis are offset by 0.4 mm. The offset causes the axial excitation rays to scatter from the meniscus with a slight angle, resulting in a tilt of the cone of scattered excitation rays 75. The outermost rays within tilted cone are collimated at a position that is further from the optical system axis than in FIG. 6A. Fortunately, the diameter of the shadow disc 57 is sufficiently large to also intercept these rays. The optical system shown in FIG. 6A is therefore robust and can tolerate lateral well misalignments of 0.4 mm, but preferably 0.25 mm.

Figure 4:
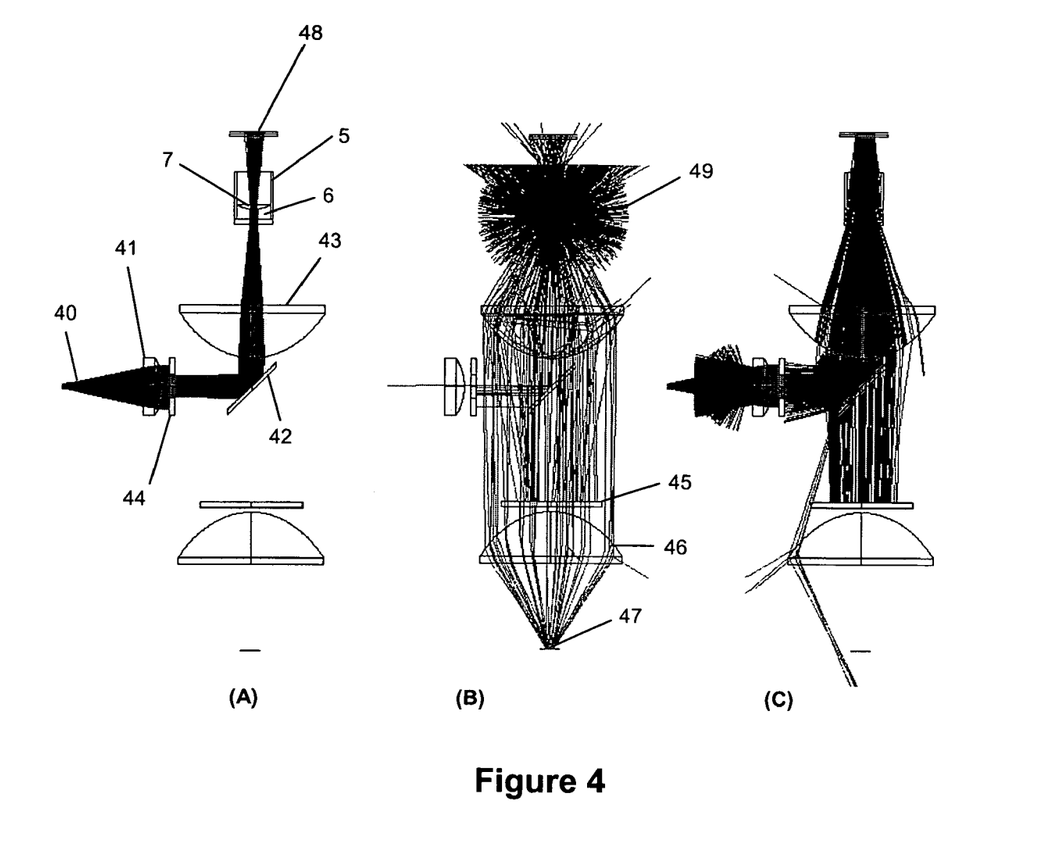
FIGS. 4A, 4B and 4C schematically illustrate the optical system of the invention with FIG. 4A showing the optical path of the excitation beam, FIG. 4B showing the ray paths of the emission light and FIG. 4C showing the ray paths scattered excitation light.
Figure 5:
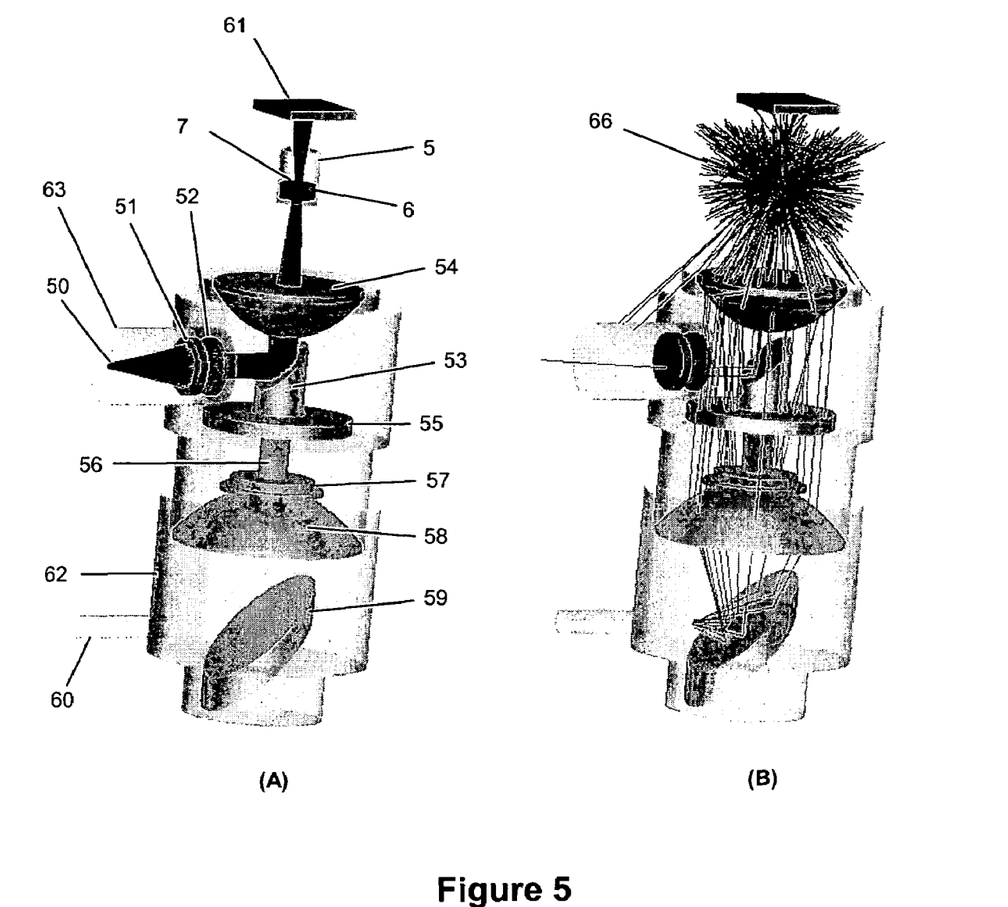
FIGS. 5A and 5B show a three-dimensional illustration of a preferred embodiment of the optical system, with FIG. 5A showing ray paths of the excitation beam and FIG. 5B showing the ray paths of the emitted light.
Figure 7:
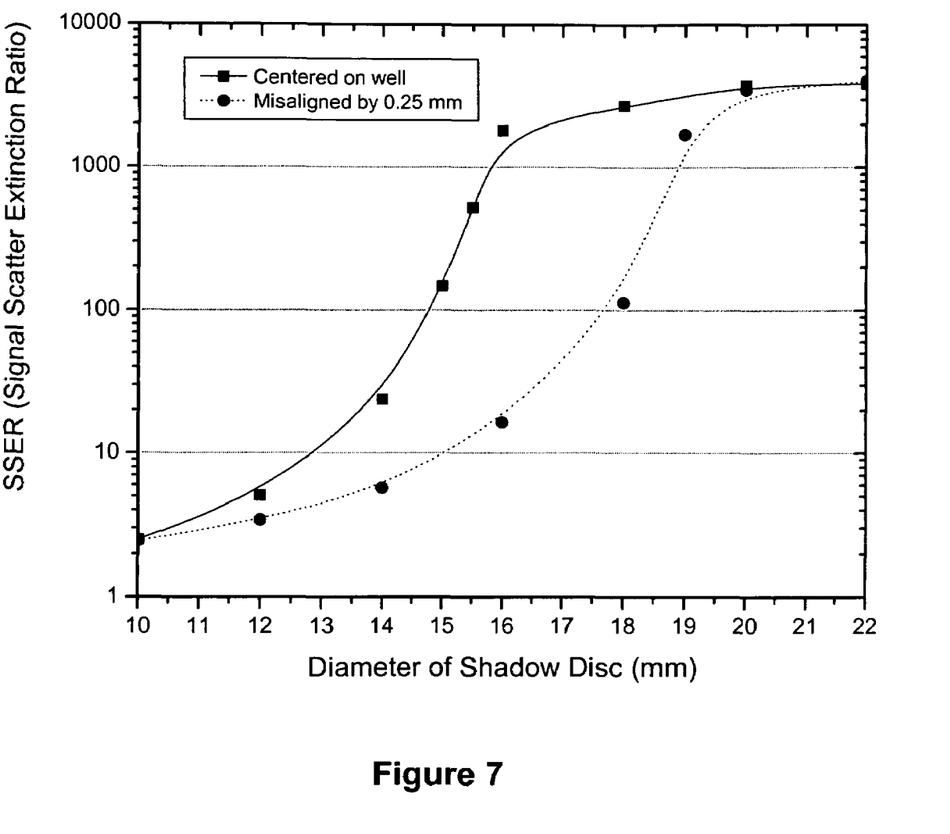
FIG. 7 shows plots of the dependence of the SSER (signal-scattering extinction ratio) on the diameter of the shadow disc.

The performance is further quantified in FIG. 7, in which the SSER is plotted as a function of the diameter of the shadow disc for the case of the preferred embodiment of FIGS. 4 and 5. A shadow disc with a 10 mm diameter, which is equal to that of the pick-off mirror 53, results in a low SSER of only 2.5. Note that if the pick-off mirror is replaced by a half-silvered mirror according to the prior art (shown in FIG. 1), then the SSER would be even lower. However, increasing the shadow disc diameter to 20 mm provides a dramatic increase in the SSER of three orders of magnitude. A diameter of 20 mm or more is also shown in FIG. 7 to maintain a SSER of greater than 1000 even if the optical head is de-centered from the well axis by 0.25 mm.

The three order of magnitude increase in the SSER produced by the present invention enhances the signal-to-noise ratio of the optical system by a corresponding three orders of magnitude, provided that scattered excitation light is limiting the system detection limit. This will often be the case for measurements in which the absorption and emission bands of the fluorophore overlap or are spectrally adjacent. Alternatively, the present invention allows the user to choose simpler and less expensive optical filters with less rejection. This novel aspect is also accompanied by the dual measurement of absorbance and fluorescence in a single optical system, which alleviates the need for a second optical beam path for absorption measurements. Finally, it is important to note that as a result of the axial beam path through the optical system, the performance is insensitive to variations in sample volume (i.e. fluid height) and different meniscus radii of curvature.

Although the examples disclosed herein pertain to measurements of fluorescence through the bottom of a microplate well, the optical head may be mounted either above or below the microplate wells. In a preferred embodiment, the position of the optical head is user-configurable and may be moved to enable reading from below or from above the wells. If the optical head is mounted below the microplate wells, then either clear (i.e. polystyrene) microplates or clear-bottom black microplates may be used. Although clear-bottom black microplates are advantageous, the efficient rejection of scattered excitation light in the optical system and confocal nature of the fluorescence measurement provides excellent performance with clear microplates as well in many cases.

The optical system may be securely mounted with the microplate reader or assay instrument, and the reading of adjacent wells be achieved by moving the microplate on a two-dimensional translation stage. In this configuration, the optical source and optical detector, and accompanying filtering elements, may be directly integrated into the optical system using methods known in the prior art. Alternatively, the compact optical head may instead be moved relative to a stationary microplate. In this configuration, the filtered excitation light from a stationary light source subsystem is preferably delivered to the optical head via fiber a fiber optic bundle. The excitation delivery bundle may be bifurcated to provide an optical power reference beam. In addition, the emission beam is preferably delivered to a stationary filtering and detection subsystem via a fiber optic bundle. Furthermore, the absorbance detector 61 is preferably mounted on a separate mechanical arm that extends around the microplate and maintains stable alignment along the vertical axis of the optical system without causing mechanical interruption.

It will be apparent to those skilled in the art that there are many possible forms of the invention that, while differing from the aforementioned embodiments, do not depart from the scope and theme of the invention. For example, the pick-off mirror 53 may be replaced by a half-silvered mirror, and the transmitted beam can be used as a reference beam for monitoring the optical power of the excitation beam. Also, the pick-off mirror may be supported on a solid platform suspended in the center of the optical system rather than resting on an optical window 55. Furthermore, the optical system may be adapted to the measurement of fluorescence and absorbance in 384-well microplates by decreasing the numerical aperture and/or focused spot size of the excitation beam.

Figure 8:
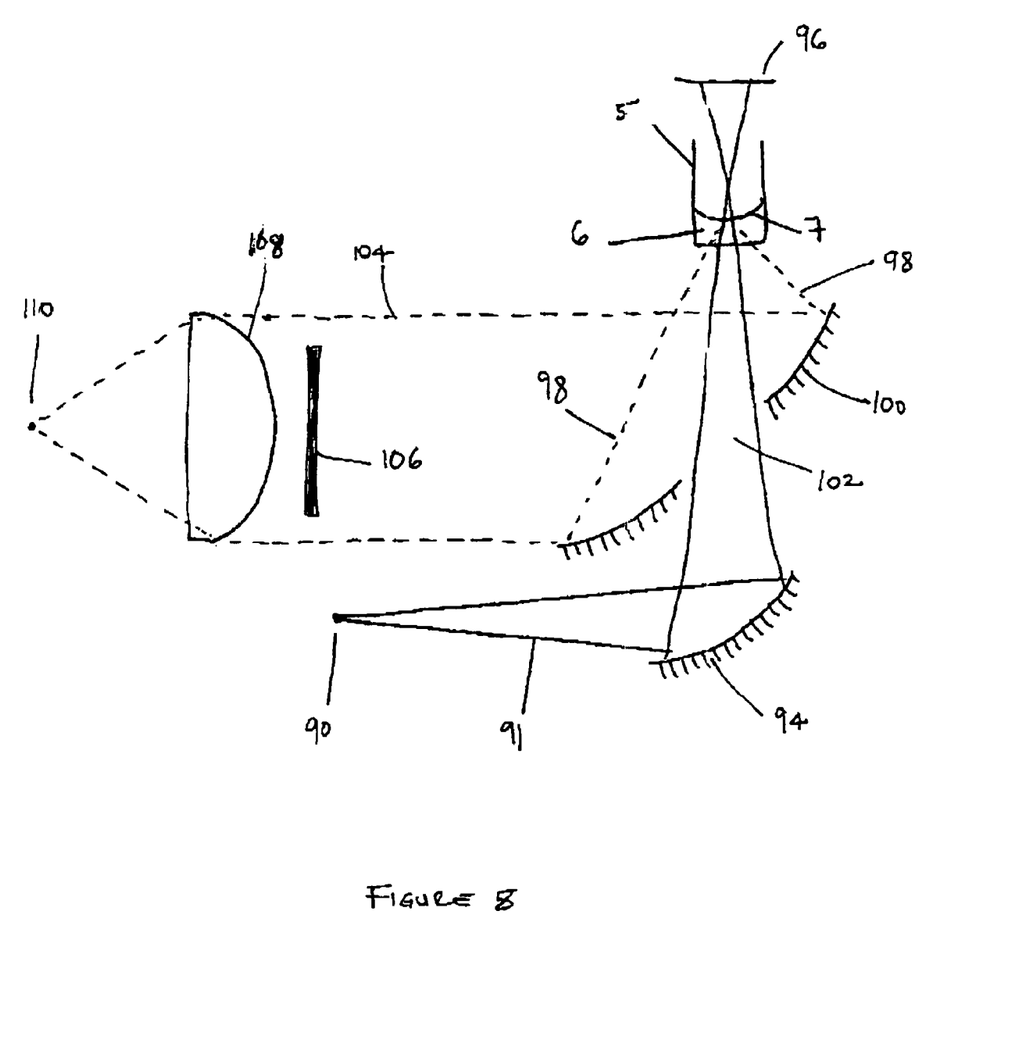
FIG. 8 shows an alternative embodiment of an optical system for reducing the intensity of scattered light from the liquid meniscus using concave mirrors.

Another modification of the above embodiments involves the use of metallic mirrors in the place of lenses. This approach has the threefold advantage of increasing the system bandwidth, reducing spurious reflections, and eliminating chromatic aberrations. Referring to FIG. 8, excitation light rays 91 from the light source 90 are focused onto the microplate well 5, along the axis of the microplate well, by a first curved mirror 94.

The optical power of the beam of excitation light is transmitted through the liquid sample is measured by a detector 96 positioned above the microplate well 5. The fluorescent light 98 emitted from the fluorescent liquid 6 is collected, collimated, and redirected by a second concave mirror 100. A hole 102 is cut through the second concave mirror 100 in order to allow the passage of the focused beam of light originating from the light source. The collimated fluorescent light 104 passes a shadow disc 106, which absorbs excitation light scattered by the meniscus 7. The ring of fluorescent light that remains after passing the shadow disc 106 is focused to a focal point 110 by an aspheric lens 108.

In a variation of this embodiment, an on-axis parabolic mirror or off-axis parabolic mirror (not shown) may be used in place of the aspheric lens 108 to focus the collimated beam after it propagates past the shadow disc 106. In a preferred embodiment, a molded glass aspheric lens 108 is used because of its low cost and because the final focusing section of the optical system is relatively immune to minor chromatic aberrations. Furthermore, since the position of the lens 108 is beyond the shadow disc 106, the effect of scattering by the lens surfaces need not be considered. Finally, since the emitted light is red-shifted from the excitation wavelength, the transmission through a glass aspheric lens is most often sufficient, even if the excitation wavelength is in the ultraviolet part of the spectrum. This arrangement provides improved optical performance over the aforementioned preferred embodiment, at the expense of the additional cost of a low numerical aperture off-axis parabolic mirror.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An optical system for measuring fluorescence from a liquid contained in a vessel, comprising:
    a) a light source and a first concave mirror for directing and focusing excitation light beam from said light source onto said vessel, along an axis of said vessel located in a vessel holder;
    b) a second concave mirror for collimating and redirecting light emitted from the liquid in said vessel along another axis, said second concave mirror being located between said vessel and said first concave mirror, said second concave mirror including a hole through which the excitation light beam reflected by the first concave mirror passes;
    c) a directing and focusing means for directing and focusing light collimated and redirected from said second concave mirror onto a first detection means; and
    d) wherein excitation light scattered from refractive surfaces within the vessel including a liquid meniscus passes through said hole, but some fluorescent light emitted by the liquid in said vessel is reflected by the second concave mirror and is focused onto the detection means by said directing and focusing means.

2. The optical system according to claim 1 including a shadow disc located between the second concave mirror and the directing and focusing means which is symmetrically disposed with respect to said another axis, wherein a diameter of said shadow disc is greater than that of said hole projected onto said another axis but less than a diameter of said second concave mirror projected onto said another axis such that some of the excitation light scattered from said refractive surfaces which does not pass through said hole is rejected by said shadow disc.

3. The optical system according to claim 1 wherein said directing and focusing means is a lens.

4. The optical system according to claim 1 wherein said directing and focusing means is a third concave mirror.

5. The optical system according to claim 1 wherein said second concave mirror is a parabolic mirror.

6. The optical system according to claim 2 wherein the diameter of said shadow disc is at least 75% that of the diameter of said second concave mirror projected onto said another axis.

7. The optical system according to claim 1 including a second detection means positioned relative to said vessel to detect excitation light transmitted through said vessel for measuring absorbance of excitation light.

8. The optical system according to claim 1 wherein said light source is a narrowband light source.

9. The optical system according to claim 1 including a bandpass filter positioned between said second concave mirror and said directing and focusing means for transmitting a pre-selected spectral band.

10. The optical system according to claim 1 wherein a focal length of said first concave mirror and a size of said light source are selected to give a diameter of the beam of excitation light at a position of the meniscus that is substantially smaller than a diameter of the meniscus.

11. The optical system according to claim 10 wherein said diameter of the beam of excitation light at a position of the meniscus is about 25% of the diameter of the meniscus.

12. The optical system according to claim 10 wherein a center of said beam of excitation light at a position of said meniscus in said vessel is substantially coincident with a center of said meniscus.

13. The optical system according to claim 12 wherein a spatial offset between said center of said beam of excitation light at a position of said meniscus in said vessel and the center of said meniscus is less than 5% of the diameter of said meniscus.

14. The optical system according to claim 1 contained in a housing, including a translation means for translating the housing in the plane that is orthogonal to the axis of the vessel.

15. The optical system according to claim 14 wherein the vessel is a microtitre plate having an array of sample wells, wherein the translation means is adapted such that each well can be individually accessed by the optical system.

16. The optical system according to claim 1 wherein a focal length and a diameter of the first concave mirror is chosen to restrict a numerical aperture of the focused beam of excitation light to less than 0.2.

17. The optical system according to claim 2 wherein a separation between said second concave mirror and said shadow disc is greater than or equal to said diameter of the second concave mirror.

18. The optical system according to claim 1 wherein the vessel located in the vessel holder is positioned relative to the beam of excitation light such that the beam of excitation light is directed to enter through a top of the vessel and first contacts the liquid meniscus and exits through a bottom of the vessel.

19. The optical system according to claim 1 wherein the vessel located in the vessel holder is positioned relative to the beam of excitation light such that the beam of excitation light is directed to enter first through a bottom of the vessel and contacts the liquid and exits through the liquid meniscus and out through a top of the vessel.

20. The optical system according to claim 2 wherein the shadow disc is made of a material which absorbs light that impinges upon it.

21. A method for measuring fluorescence from a liquid contained in a vessel, comprising:
   a) directing and focusing excitation light from a light source onto a vessel along an axis of said vessel using a first concave mirror;
   b) collecting, collimating and redirecting light emitted from the liquid in said vessel along another axis using a second concave mirror, said second concave mirror being located between said vessel and said first concave mirror, said second concave mirror including a hole through which the excitation light beam reflected by the first concave mirror passes; and
   c) directing and focusing light collimated and redirected from said second concave mirror onto a first detection means, wherein excitation light scattered from refractive surfaces within the vessel including a liquid meniscus passes through said hole, but some fluorescent light emitted by the liquid in said vessel is reflected by the second concave mirror and is focused onto the detection means by said directing and focusing means.

22. The method according to claim 21 including a shadow disc located between the second concave mirror and the directing and focusing means which is symmetrically disposed with respect to said another axis, wherein a diameter of said shadow disc is greater than that of said hole projected onto said another axis but less than a diameter of said second concave mirror projected onto said another axis such that some of the excitation light scattered from said refractive surfaces which does not pass through said hole is rejected by said shadow disc.

23. The method according to claim 22 wherein said directing and focusing means is a lens.

24. The method according to claim 22 wherein said directing and focusing means is a third concave mirror.

25. The method according to claim 22 wherein said second concave mirror is a parabolic mirror.

26. The method according to claim 22 wherein the diameter of said shadow disc is at least 75% that of the diameter of said second concave mirror projected onto said another axis.

27. The method according to claim 21 including a second detection means positioned relative to said vessel to detect excitation light transmitted through said vessel for measuring absorbance of excitation light.

* * * * *